(12) United States Patent
Fosdick et al.

(10) Patent No.: US 8,937,196 B2
(45) Date of Patent: Jan. 20, 2015

(54) PROCESS FOR REMOVING AN IMPURITY FROM A SILOXANE

(75) Inventors: Robert Fosdick, Midland, MI (US); Stephen Kamin, Midland, MI (US); Hanh Vo, Midland, MI (US); Tylyn Weickert, Union, KY (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 13/877,468

(22) PCT Filed: Nov. 14, 2011

(86) PCT No.: PCT/US2011/060544
§ 371 (c)(1),
(2), (4) Date: Apr. 3, 2013

(87) PCT Pub. No.: WO2012/067988
PCT Pub. Date: May 24, 2012

(65) Prior Publication Data
US 2013/0225848 A1    Aug. 29, 2013

Related U.S. Application Data

(60) Provisional application No. 61/414,018, filed on Nov. 16, 2010.

(51) Int. Cl.
| | | |
|---|---|---|
| *C07F 7/20* | (2006.01) | |
| *B01D 11/04* | (2006.01) | |
| *C08G 77/34* | (2006.01) | |
| *B01J 20/28* | (2006.01) | |

(52) U.S. Cl.
CPC . *C07F 7/20* (2013.01); *B01D 11/04* (2013.01); *C08G 77/34* (2013.01); *B01J 20/28023* (2013.01); *B01J 20/28004* (2013.01)
USPC ............................ 556/466; 556/482; 210/316

(58) Field of Classification Search
USPC .................................... 556/466, 482; 210/316
See application file for complete search history.

(56) References Cited

U.S. PATENT DOCUMENTS

| | | | |
|---|---|---|---|
| 3,977,829 A | 8/1976 | Clonts | |
| 3,992,156 A * | 11/1976 | Clonts | .......................... 422/256 |
| 5,997,731 A | 12/1999 | Suarez | |
| 6,451,906 B1 * | 9/2002 | Saito et al. | .................... 524/588 |
| 7,618,544 B2 | 11/2009 | Massingill, Jr. | |
| 7,833,499 B2 * | 11/2010 | Zang et al. | ................... 423/183 |
| 8,128,825 B2 | 3/2012 | Massingill | |
| 2012/0209014 A1 | 8/2012 | Massingill | |

FOREIGN PATENT DOCUMENTS

EP    1362878 B1    4/2006

* cited by examiner

*Primary Examiner* — Sudhakar Katakam
*Assistant Examiner* — Pancham Bakshi
(74) *Attorney, Agent, or Firm* — Catherine U. Brown

(57) ABSTRACT

A process for removing an impurity from a siloxane comprising i) flowing a first liquid through a fiber bundle comprising a plurality of fibers extending lengthwise in a conduit, wherein the bundle has an upstream end and a downstream end, and the first liquid flows in a direction from the upstream end of the bundle to the downstream end; and ii) while continuing (i), flowing a second liquid comprising a siloxane and an impurity through the fiber bundle in a direction from the upstream end of the bundle to the downstream end of the bundle to effect transfer of at least a portion of the impurity from the second liquid to the first liquid, wherein the first liquid and the second liquid are substantially immiscible.

21 Claims, 1 Drawing Sheet

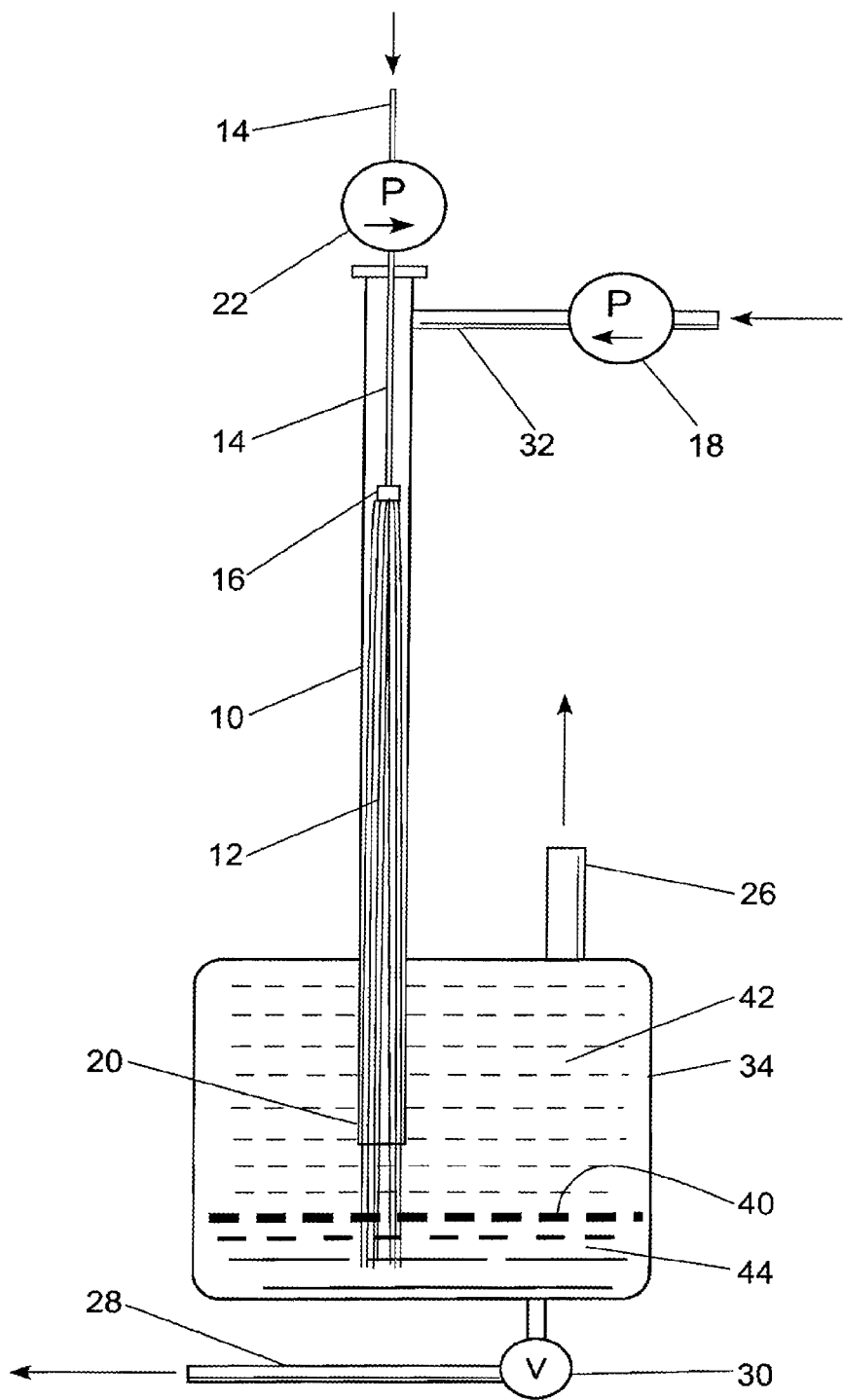

PROCESS FOR REMOVING AN IMPURITY FROM A SILOXANE

CROSS REFERENCE TO RELATED APPLICATIONS

This application is a U.S. national stage filing under 35 U.S.C. §371 of PCT application Ser. No. PCT/US11/60544 filed on Nov. 14, 2011, currently pending, which claims the benefit of U.S. Provisional Patent Application No. 61/414018 filed Nov. 16, 2010 under 35 U.S.C. §119 (e). PCT Application No. PCT/US11/60544 and U.S. Provisional Patent Application No. 61/414018 are hereby incorporated by reference.

FIELD OF THE INVENTION

The present invention relates to a process for removing at least a portion an impurity from a siloxane by flowing a first liquid and a second liquid, the latter comprising a siloxane and an impurity, through a fiber bundle, wherein the first liquid and second liquid are substantially immiscible.

BACKGROUND OF THE INVENTION

Used in a wide range of applications and industries from automotive to personal care, siloxanes are typically made by the hydrolysis of halosilanes or organohalosilanes. After hydrolysis, the siloxanes typically comprise residual impurities, such as acid or salt, which can be detrimental to the stability and performance of the siloxanes in various applications and which can be difficult to remove. For example, residual hydrogen chloride can potentially contribute to discoloration and viscosity increase upon aging.

Impurities have been removed in the past by traditional techniques involving dispersing the siloxane in an immiscible solvent, such as water, allowing the two immiscible liquids to coalesce and separate, and then removing the siloxane and solvent layers separately. However, dispersing the siloxane in solvent to the small droplet sizes necessary to provide an adequate interface between the two liquids requires large amounts of energy, and the coalescing and separating steps can require significant amounts of time. In addition, the removal efficiency is limited.

Therefore, there is a need for new methods of removing an impurity from a siloxane that require less energy, avoid lengthy coalescing and separation steps, and effectively remove the impurity.

BRIEF SUMMARY OF THE INVENTION

The present invention is directed to a process for removing an impurity from a siloxane comprising i) flowing a first liquid through a fiber bundle comprising a plurality of fibers extending lengthwise in a conduit, wherein the bundle has an upstream end and a downstream end, and the first liquid flows in a direction from the upstream end of the bundle to the downstream end; and ii) while continuing (i), flowing a second liquid comprising a siloxane and an impurity through the fiber bundle in a direction from the upstream end of the bundle to the downstream end of the bundle to effect transfer of at least a portion of the impurity from the second liquid to the first liquid, wherein the first liquid and the second liquid are substantially immiscible.

The process of the present invention allows for the quick removal of at least a portion of an impurity from a siloxane and the fast separation of the siloxane from the liquid. The process does not require the mechanical mixing, and therefore the energy, of traditional extraction methods.

The purified siloxanes produced by the invention are used in a broad spectrum of applications and industries from automotive to personal care.

BRIEF DESCRIPTION OF THE DRAWINGS

FIG. 1 is a diagram of an apparatus for removing a impurity from a siloxane according to the present invention.

DETAILED DESCRIPTION OF THE INVENTION

A process for removing an impurity from a siloxane, the process comprising:

i) flowing a first liquid through a fiber bundle comprising a plurality of fibers extending lengthwise in a conduit, wherein the bundle has an upstream end and a downstream end, and the first liquid flows in a direction from the upstream end of the bundle to the downstream end; and ii) while continuing (i), flowing a second liquid comprising a siloxane and an impurity through the fiber bundle in a direction from the upstream end of the bundle to the downstream end of the bundle to effect transfer at least a portion of the impurity from the second liquid to the first liquid, wherein the first liquid and the second liquid are substantially immiscible.

In step i) a first liquid is flowed through a fiber bundle comprising a plurality of fibers extending lengthwise in a conduit, wherein the bundle has an upstream end and a downstream end, and the first liquid flows in a direction from the upstream end of the bundle to the downstream end.

The first liquid typically comprises a polar solvent. The polar solvent may be any polar protic or polar aprotic solvent. As used herein, "polar" means having a dielectric constant of at least 15 at 20° C. Examples of polar solvents include, but are not limited to, water; water solutions, including acid and base (e.g., KOH or NaOH) solutions; alcohols, including ethanol, propanol, isopropanol, and butanol; phenols; amines, including polyamines, ethanolamines, and polyethanolamines; carboxylic acids; dimethyl sulfoxide; ketones such as acetone; and ionic liquids, including 1-allyl-3-methylimidazolium chloride, 1-ethyl-3-methylimidazolium tetrafluoroborate, 1,2-dimethyl-3-n-propylimidazolium tetrafluoroborate, 1,2-dimethyl-2-n-butylimidazolium tetrafluoroborate, and 1,2-dimethyl-3-n-butylimidazolium hexafluorophosphate. In one embodiment, the first liquid comprises water. The first liquid may be a mixture of polar solvents.

The fibers in the fiber bundle are selected to be preferentially wetted by the first liquid versus the second liquid, the latter described below. The fibers typically do not also add contaminates to the siloxane and typically are able to withstand the process to prevent frequent replacement.

Examples of fibers include, but are not limited to, fibers comprising cotton, jute, silk, treated minerals, untreated minerals, metals, metal alloys, treated carbon, untreated carbon, polymers, and polymer blends. Suitable treated or untreated mineral fibers include, but are not limited to, fibers of glass, asbestos, ceramics, and combinations thereof. Suitable metal fibers include, but are not limited to, fibers of iron, steel, nickel, copper, brass, lead, tin, zinc, cobalt, titanium, tungsten, nichrome, silver, aluminum, magnesium, and alloys thereof. Suitable polymer fibers include, but are not limited to, fibers of hydrophilic polymers, polar polymers, hydrophilic copolymers, polar copolymers, and combinations thereof, such as polysaccharides, polypeptides, polyacrylic acid, polymethacrylic acid, functionalized polystyrene (including sulfonated polystyrene and aminated polystyrene), nylon, polybenzimidazole, polyvinylidenedinitrile, polyvinylidene chloride, polyphenylene sulfide, polymelamine, polyvinyl chloride, co-polyethylene-acrylic acid and ethylene-vinyl alcohol copolymers. In one embodiment, the fibers comprise glass or steel fibers.

The diameter of the fibers forming the fiber bundle is typically from 1 to 100 μm, alternatively from 5 to 25 μm, alternatively from 8 to 12 μm.

Combinations of fibers may be employed. The fibers may be made by methods known in the art. Many of these fibers are available commercially.

The fiber bundle may be formed in the conduit, described below, by methods known in the art. For example, a group of the fibers may be hooked at the middle with a wire and pulled into the conduit using the wire.

The conduit is typically cylindrically shaped and comprised of a non-reactive material, such as stainless steel or Teflon. The conduit is typically part of a mass transfer apparatus comprising fibers. Mass transfer apparatuses comprising fibers are known in the art. For example, mass transfer apparatuses have been described in U.S. Pat. Nos. 3,977,829, 5,997,731, and 7,618,544.

An apparatus comprising a conduit is depicted in FIG. 1; however, the invention is not intended to be limited to such apparatus. One skilled in the art will readily envision other acceptable design variations for the apparatus based on this description. In FIG. 1, conduit 10 has in it a fiber bundle 12 filling the conduit 10 for a portion of its length. The fiber bundle 12 is in contact with and extends into tube 14 at end 16. Tube 14 extends beyond the end of the conduit 10 and has metering pump 22 associated with it to pump a first liquid through tube 14 and onto the fiber bundle 12. Connected to conduit 10, upstream of the end 16 of tube 14, is an inlet pipe 32 having associated with it a metering pump 18. Pump 18 supplies a second liquid through inlet pipe 32 and into conduit 10, where it flows between fiber bundle 12. At the downstream end of the conduit 10 is a collection vessel 34 into which the downstream end 20 of conduit 10 and fiber bundle 12 may extend. The first and second liquids flow into collection vessel 34 and form layers 42 and 44. Fiber bundle 12 extends out of the downstream end 20 of conduit 10 into collection vessel 34 and first layer 44. Associated with an upper portion of collection vessel 34 is an outlet line 26 for top layer 42, and associated with a lower portion of collection vessel 34 is an outlet 28 for bottom layer 44. There is a metering valve 30 in outlet 28. In one embodiment (not shown), the apparatus is also equipped with means of controlling the temperature within the conduit. For example, the apparatus may be equipped with a heat exchanger or a heating jacket.

The temperature of the first liquid introduced in step i) is not critical and can vary from greater than the freezing point temperature to less than the boiling point temperature of the first liquid. For example, when the first liquid is water, the temperature is typically from greater than 0° C. to less than 100° C.; alternatively from 15 to 80° C.; alternatively from 15 to 60° C. at standard pressure.

The pressure at which the first liquid is introduced is typically atmospheric pressure or greater than atmospheric pressure. For example, the first liquid is typically introduced at a pressure from 0 to 1000 kilopascals gauge (kPag), alternatively from 0 to 800 kPag.

The viscosity is sufficient so that the first liquid flows through the fiber bundle. For example, a sufficient viscosity of the first liquid is typically from 0.1 to 500 cSt, alternatively from 0.1 to 100 cSt, alternatively from 0.1 to 50 cSt, alternatively from 0.1 to 10 cSt, at 25° C.

In step (ii), a second liquid, comprising a siloxane and an impurity, is flowed through the fiber bundle, while continuing (i), in a direction from the upstream end of the bundle to the downstream end of the bundle to effect transfer of the impurity from the second liquid to the first liquid, wherein the first liquid and the second liquid are substantially immiscible.

The siloxane is a compound containing at least one Si—O—Si linkage and may be a solid or a liquid. There is typically no limit on the viscosity or molecular weight of the siloxane. For example the molecular weight of the siloxane is typically at least 75 grams/mole, alternatively at least 500 grams/mole, alternatively from 500 to 25,000 grams/mole. At least one silicon atom in the siloxane may be substituted with an element selected from carbon, boron, aluminum, titanium, tin, lead, phosphorus, arsenic, and other elements.

The siloxane may be a disiloxane, a trisiloxane, or other polysiloxane. Polysiloxane compositions may have a linear, branched, cyclic, or cross-linked (e.g., resinous) structure and are typically hydroxy- or methyl-endblocked.

The polysiloxane typically contains at least some portion that may be considered as an organopolysiloxane segment. Organopolysiloxanes are polymers containing siloxy units independently selected from $(R_3SiO_{1/2})$, $(R_2SiO_{2/2})$, $(RSiO_{3/2})$, or $(SiO_{4/2})$ siloxy units, where each R independently may be H or any monovalent organic group, alternatively each R is independently H, hydrocarbyl containing 1 to 20 carbon atoms, or substituted hydrocarbyl containing 1 to 20 carbon atoms, alternatively each R is independently an alkyl group containing 1 to 20 carbon atoms, alternatively R is methyl. These siloxy units are commonly referred to as M, D, T, and Q units respectively. Their molecular structures are listed below:

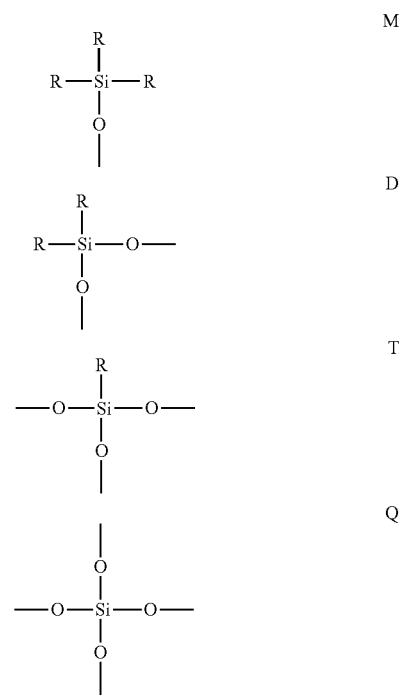

The polysiloxane may also contain organic segments which comprise units selected from $—(CR_2)—$, and $—(CR_3)—$, where R is as defined and exemplified above.

The polysiloxane may be a silicone fluid, a silicone resin, or an organosilicon polymers. Silicone fluids and silicone resins typically have structural units according to the formula $(R_nSi-O_{(4-n)/2})$, where n has an average value of at least 2 for silicone fluids and less than 2 for silicone resins and R is as described above; organosilicon copolymers typically have structural units according to the formulas $(R_nSi-O_{(4-n2)})$, where n is from 0 to 3 and R is as described above, and $CR_2$, where R is as defined and exemplified above.

The hydrocarbyl groups represented by R typically have from 1 to 20 carbon atoms, alternatively from 1 to 10 carbon atoms, alternatively from 1 to 4 carbon atoms. Acyclic hydrocarbyl groups containing at least three carbon atoms can have a branched or unbranched structure. Examples of hydrocarbyl groups include, but are not limited to, alkyl such as methyl, ethyl, propyl, 1-methylethyl, butyl, 1-methylpropyl, 2-methylpropyl, 1,1-demethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, and decyl; cycloalkyl such as cyclopentyl, cyclohexyl, and methylcyclohexyl; aryl such as phenyl or naphthyl; alkenyl groups such as vinyl, allyl, 5-hexenyl, and cyclohexenyl; alkaryl such as tolyl and xylyl, arylalkyl such as benzyl, phenethyl, phenpropyl, and phenylhexyl; and aralkenyl, such as styryl and cinnamyl, and alkynyl, such as ethynyl and propynyl. One skilled in the art will appreciate that some of the R groups on the organopolysiloxanes units described above may be groups other than those specifically defined above, such as, for example, hydroxyl groups in the case of hydroxyl end-blocking.

The substituted hydrocarbyl groups represented by R typically have from 1 to 20 carbon atoms, alternatively from 1 to 10 carbon atoms, alternatively from 1 to 4 carbon atoms. Examples of the substituted hydrocarbyl groups include, but are not limited to, the hydrocarbyl groups described and exemplified above for R substituted with a substituent. Examples of a substituent include, but are not limited to —F, —Cl, —Br, —I, —OH, —OCH$_3$, —OCH$_2$CH$_3$, —OCH$_2$CH$_2$OCH$_2$CH$_3$, and fluorocarbons including, for example 3,3,3-trifluoropropyl groups —CF$_3$.

Examples of the polysiloxane include, but are not limited to, trimethylsiloxy-terminated polydimethylsiloxane, triethylsiloxy-terminated polydimethylsiloxane, dimethylhydroxysiloxy-terminated polydimethylsiloxane, diethylhydroxysiloxy-terminated polydimethylsiloxane, diphenyl(methyl)siloxy-terminated polymethyl(phenyl)siloxane, trimethylsiloxy-terminated polydimethylsiloxane-polymethylvinylsiloxane copolymers, vinyldimethylsiloxy-terminated polydimethylsiloxane-polymethylvinylsiloxane copolymers, trimethylsiloxy-terminated polydimethylsiloxane-polymethylhexenylsiloxane copolymers, hexenyldimethylsiloxy-terminated polydimethylsiloxane-polymethylhexenylsiloxane copolymers, vinyldimethylsiloxy-terminated polydimethylsiloxane-polymethyhexenylsiloxane copolymers, trimethylsiloxy-terminated polymethylvinylsiloxane polymers, trimethylsiloxy-terminated polymethylhexenylsiloxane polymers, vinyldimethylsiloxy-terminated polydimethylsiloxane polymers, and hexenyldimethylsiloxy-terminated polydimethylsiloxane polymers, vinyldimethylsiloxy-terminated poly(dimethylsiloxane-monomethylsilsesquioxane) polymers, trimethylsiloxy-terminated poly(dimethylsiloxane-methylsilsesquioxane) copolymers, vinyldimethylsiloxy-terminated poly(dimethylsiloxane-vinylmethylsiloxane-methylsilsesquioxane) copolymers; trimethylsiloxy terminated poly(dimethylsiloxane-vinylmethylsiloxane-methylsilsesquioxane) polymers, hexenyldimethylsiloxy terminated poly(dimethylsiloxane-monomethylsilsesquioxane) polymers, hexenyldimethylsiloxy terminated poly(dimethylsiloxane-hexenylmethylsiloxane-methylsilsesquioxane) copolymers, trimethylsiloxy terminated poly(dimethylsiloxane-hexenylmethylsiloxane-methylsilsesquioxane) polymers, vinyldimethylsiloxy terminated poly(dimethylsiloxane-silicate) copolymers, hexenyldimethylsiloxy-terminated poly(dimethylsiloxane-silicate) copolymers, trimethylsiloxy terminated poly(dimethylsiloxane-vinylmethylsiloxane-silicate) copolymers and trimethylsiloxy terminated poly(dimethylsiloxane-hexenylmethylsiloxane-silicate) copolymers, vinylsiloxy or hexenylsiloxy terminated poly(dimethylsiloxane-hydrocarbylene copolymers), vinylsiloxy terminated or hexenylsiloxy terminated poly(dimethylsiloxane-polyoxyalkylene) block copolymers, alkenyloxydimethylsiloxy terminated polyisobutylene, alkenyloxydimethylsiloxy terminated polydimethylsiloxane-polyisobutylene block copolymers, hexamethylcyclotrisiloxane, octamethylcyclotetrasiloxane, decamethylcyclopentasiloxane, dodecamethylcyclohexasiloxane, silicone resins sold under the trademarks DOW CORNING® 840 Resin, DOW CORNING® 2-7466 Resin, DOW CORNING® 2-9138 Resin, DOW CORNING® 2-9148 Resin, DOW CORNING® 2104 Resin , DOW CORNING® 2106 Resin, DOW CORNING® 217 Flake Resin, DOW CORNING® 220 Flake Resin, DOW CORNING® 233 Flake Resin, DOW CORNING® 4-2136 Resin, and polysilylenesiloxanes, such as trimethylsilyl- and trimethylsiloxy-terminated polysilylenedimethylsiloxane.

The siloxane is typically prepared by known methods to hydrolyze any suitable halosilane. The halosilane typically has the formula $R_aSiX_{4-a}$, wherein each R is as described and exemplified above, X is $C_1$-$C_8$ alkoxy or halo, for example, chloro, bromo, or iodo, and a is an integer from 0 to 3.

The alkoxy groups represented by X typically have from 1 to 8 carbon atoms, alternatively from 1 to 4 carbon atoms. Examples of alkoxy groups include, but are not limited to methoxy, ethoxy, propoxy, and butoxy.

Examples of suitable halosilanes that can be hydrolyzed to make the siloxane include, but are not limited to, diorganodihalosilane compounds such as dimethyldichlorosilane $(CH_3)_2SiCl_2$, diethyldichlorosilane $(C_2H_5)_2SiCl_2$, di-n-propyldichlorosilane (n-$C_3H_7$)$_2$SiCl$_2$, di-i-propyldichlorosilane (i-$C_3H_7$)$_2$SiCl$_2$, di-n-butyldichlorosilane (n-$C_4H_9$)$_2$SiCl$_2$, di-i-butyldichlorosilane (i-$C_4H_9$)$_2$SiCl$_2$, di-t-butyldichlorosilane (t-$C_4H_9$)$_2$SiCl$_2$), n-butylmethyldichlorosilane CH$_3$(n-$C_4H_9$)SiCl$_2$, octadecylmethyldichlorosilane CH$_3$(C$_{18}$H$_{37}$)SiCl$_2$, diphenyldichlorosilane $(C_6H_5)_2SiCl_2$, phenylmethyldichlorosilane CH$_3$(C$_6$H$_5$)SiCl$_2$ and dicyclohexyldichlorosilane (C$_6$H$_{11}$)$_2$SiCl$_2$; organohydrodihalosilane compounds such as methyldichlorosilane, CH$_3$HSiCl$_2$, and any of the diorganodihalosilanes listed above in which one of the alkyl substituents is replaced by hydrogen; triorganohalosilane compounds such as trimethylchlorosilane (CH$_3$)$_3$SiCl; and organotrihalosilane compounds such as methyltrichlorosilane.

The siloxane may be a single siloxane or a mixture of siloxanes. Many of the siloxanes of the invention are available commercially.

The impurity is any material that is extractable from the second liquid by the first liquid. Examples of the impurity include, but are not limited to, acids, such as hydrogen chloride, hydrogen bromide, hydrogen iodide, acetic acid, and trifluoromethane sulfonic acid; salts, such as sodium chloride, potassium chloride, sodium bromide, potassium bromide, sodium trifluoroacetate, and potassium trifluoroacetate; ions, such as Cl⁻, Br⁻, Na⁺, and K⁺; and linear and cyclic siloxanes with a molecular weight less than 500 g/mole.

The concentration of the impurity in the second liquid is typically as least 3 parts per million by weight (ppmw), based on the weight of the impurity and the siloxane, alternatively from 10 to 10,000 parts per million by weight (ppmw), alternatively from 10 to 5000 ppmw, alternatively from 50 to 1500 ppmw, on the same basis.

The second liquid may further comprise an optional non-polar solvent that is miscible with the siloxane. The non-polar solvent may be included to, for example, dilute a siloxane of high viscosity or dissolve a solid siloxane. For example, the second liquid may comprise at least 10% (w/w), alternatively at least 25% (w/w), alternatively from 40 to 90% (w/w), based on the combined weight of the non-polar solvent and the siloxane, of the non-polar solvent.

Examples of non-polar solvents include, but are not limited to, aromatic solvents, such as xylene; aliphatic solvents, such as pentane, hexane, heptane, octane, isoalkanes or blends of isoalkanes, such as a blend of $C_9$-$C_{19}$ isoalkanes or and $C_{12}$-$C_{18}$ isoalkanes; and siloxanes, such as hexamethyldisiloxane. In one embodiment, the second liquid further comprises hexamethyldisiloxane.

The viscosity of the second liquid is sufficient for the second liquid to flow through the conduit. For example, the viscosity of the second liquid is typically less than 500 centistokes (cSt), alternatively from 0.1 to 500 cSt, alternatively from 0.1 to 100 cSt, alternatively from 0.1 to 50 cSt, alternatively from 0.1 to 10 cSt, at 25° C. The viscosity of the second liquid can be controlled by dissolving higher viscosity or solid siloxanes in a suitable non-polar solvent as described above.

The volumetric flow ratio of the second liquid to the first liquid is typically as least 0.1, alternatively from 0.1 to 20, alternatively from 1 to 4, alternatively about 3. As used herein, "volumetric flow ratio" means the ratio of the volumetric flow rate of the second liquid to that of the first liquid.

The temperature and pressure at which the second liquid is introduced is as described for the first liquid.

The second liquid is substantially immiscible with the first liquid. As used herein, "substantially immiscible" means that the second liquid will not dissolve uniformly in the first liquid, and the second liquid will form, with the first liquid, two layers. The use of "substantially" is intended to include embodiments where the first or second liquid may have some slight miscibility.

The second liquid, together with the first liquid, has a residence time that is sufficient to remove at least a portion of the impurity from the second liquid. For example, a sufficient residence time is typically at least 5 s, alternatively from 5 s to 30 minutes; alternatively from 30 s to 15 min; alternatively from 1 min to 10 min. As used herein, "residence time" means the time for one conduit volume (i.e., the volume of liquid that can fill the conduit comprising the fiber bundles) of the first liquid and second liquid together to pass through the conduit containing fibers.

The first liquid and second liquid may be flowed into the conduit by gravity or a pump.

The process of the invention may further comprise iii) receiving the first liquid and the second liquid in a collection vessel, wherein the first liquid forms a first layer and the second liquid forms a second layer in the collection vessel.

The first layer is typically the bottom layer and comprises the polar solvent and the impurity removed from the second liquid. The second layer is typically the top layer and comprises the siloxane from the second liquid. However, the position of the first layer and second layer in the collection vessel may be reversed.

The concentration of the impurity in the second layer is less than the concentration in the second liquid when initially introduced. For example, the concentration of the impurity in the second layer is typically from 0 to 50%, alternatively from 0.01 to 40%, alternatively from 0.01 to 30%, alternatively from 0.01 to 10%, of the initial concentration in the second liquid.

The collection vessel may be a gravity separator or settling tank or any other vessel that will allow for the collection and separation of the first and second liquids exiting the apparatus.

Step i) is typically conducted prior to, and during, step (ii). The collection of the first and second liquids in optional step iii) typically begins after step (i) and continues until the first liquid and second liquid cease to flow out of the conduit.

The process of the invention may further comprise iv) separating the first and second layer. The first and second layer may be separated by withdrawing the first layer and the second layer separately from the collection vessel. The first layer and second layer may be withdrawn from the collection vessel with the aid of a pump.

The process of the invention may also comprise feeding the siloxane phase separated in step iv) to the same, or another, apparatus for the further removal of at least another portion of the impurity.

Where the second layer comprises a mixture of siloxanes, the process of the invention may also comprise separating the siloxanes. The siloxanes may be separated by, for example, distillation.

The process of the invention effectively removes at least a portion of a impurity from a siloxane. The process allows for quick removal of the impurity and quick separation of the siloxane and polar solvent.

The siloxanes produced by the process of the invention may be used in established industries from the personal care to the automotive industries.

EXAMPLES

The following examples are presented to better illustrate the method of the present invention, but are not to be considered as limiting the invention, which is delineated in the appended claims. Unless otherwise noted, all parts and percentages reported in the examples are by weight. The following table describes the abbreviations used in the examples:

TABLE 1

List of abbreviations used in the examples.

| Abbreviation | Word |
|---|---|
| g | gram |
| wt | weight |
| % | percent |
| mol | mole |
| hr | hour |
| ° C. | degrees Celsius |
| mL | milliliters |
| cm | centimeter |
| HCl Removal Efficiency (%) | $([HCl]_b - [HCl]_a)/[HCl]_b \times 100$, where $[HCl]_b$ is the hydrochloric acid concentration in the siloxane before treatment; and $[HCl]_a$ is the hydrochloric acid concentration in the siloxane after treatment. |

TABLE 1-continued

List of abbreviations used in the examples.

| Abbreviation | Word |
|---|---|
| DI | deionized |
| Mw | weight average molecular weight |
| cSt | centistokes |
| ppmw | parts per million by weight |
| isoalkane | blend of $C_{12}$-$C_{18}$ isoalkanes |

Example 1

This example illustrates the use of a apparatus according to FIG. 1 to treat a dimethylsiloxane stream with deionized water to remove hydrochloric acid from the dimethylsiloxane. The apparatus of this example comprised a 1.27 cm nominal inner diameter stainless steel conduit of length 30.48 cm containing approximately 65,000 Glass Wool Pyrex fibers (Catalog #32848-003, Van Waters and Rogers, Redmond, Wash.). The fibers were 8 μm in diameter, approximately 41 cm in length, packed tightly along the entire length of the conduit, and had approximately 10 cm extending out of the downstream end of the conduit into a separatory funnel. A 1.27 cm stainless steel tee was attached to the inlet end of the conduit and deionized water and dimethylsiloxane feed lines attached.

DI water flow was introduced into the apparatus conduit at the upstream end of the Pyrex glass fibers as the first liquid. After the DI water flow was started, a second liquid comprising dimethylsiloxane (15 cSt at 25° and comprising 55% cyclic siloxane and 45% hydroxyl endblocked linear polydimethylsiloxane with a number average molecular weight equal to about 2500) containing HCl was introduced into the conduit at the upstream end of the fibers through the side inlet of the tee. The DI water first liquid and dimethylsiloxane second liquid were collected in the separatory funnel at the downstream end of the fibers. Four experimental runs were performed varying the contact time. The flow rate ratio of the dimethylsiloxane to DI water was kept constant at 4:1. The DI water and dimethylsiloxane streams exited the conduit as separate phases. No settling time was required in the separatory funnel as there was instantaneous separation of the polydimethylsiloxane and water phases. Samples of the polydimethylsiloxane stream prior to entering the conduit and from the collection vessel were titrated with potassium hydroxide using bromocresol purple indicator to determine the acid concentration. All testing was performed at 25° C. The flow rates, pressures, contact time and HCl removal efficiency are listed in Table 2.

TABLE 2

Treatment of polydimethylsiloxane containing HCl with DI water in an apparatus comprising glass fibers.

| DI Water flowrate (ml/min) | Dimethylsiloxane flowrate (ml/min) | DI water line pressure (psig) | Dimethylsiloxane line pressure (psig) | Residence Time (min.) | HCl removal efficiency (%) |
|---|---|---|---|---|---|
| 1 | 4 | 0 | 0 | 7.52 | 99.9 |
| 4 | 16 | 6 to 10 | 6 | 1.88 | 97.3 |
| 1 | 4 | 0 | 0 | 7.52 | 99.3 |
| 1 | 4 | 0 | 0 | 7.52 | 99.9 |

Example 2

The apparatus, reactants and procedure were as described in example 1 except as follows. Stainless steel fibers from Bekaert were used. The fibers were 316 L grade steel, 12 μm in diameter, and 41 cm long. Approximately 190,000 of the fibers were packed into the length of the conduit. The temperature of the dimethylsiloxane stream was maintained at 60° C. The parameters varied and the results are listed in Table 3.

TABLE 3

Polydimethylsiloxane HCl removal with DI water in a conduit comprising stainless steel fibers.

| DI Water flow rate (ml/min) | Dimethylsiloxane flow rate (ml/min) | DI water line pressure (psig) | Dimethylsiloxane line pressure (psig) | Residence time (min.) | HCl removal efficiency (%) |
|---|---|---|---|---|---|
| 1 | 4 | 0 | 0 | 6.41 | 91.5 |
| 4 | 16 | 10 | 10 to 12 | 1.60 | 85.3 |
| 2.5 | 10 | 6 to 9 | 6 to 9 | 2.57 | 75.9 |

Example 3

The apparatus, reactants and procedure described in example 1 were used except a 1.27 cm outer diameter, 40.64 cm long Teflon-FEP tube was used as the conduit, tap water was used as the first liquid, and a mixture of silicon resin (DOW CORNING 407, which has a molecular weight (Mw) equal to 21,000) and hexamethyldisiloxane (DOW CORNING 200 Fluid 0.65 cSt, Dow Corning, Midland, Mich.) was the second liquid. (The mixture had a viscosity of 5 cSt at 21° C.) The Pyrex fibers used were 60.96 cm long, with approximately 10 cm extending out the downstream end of the conduit into the collection vessel. The parameters varied are indicated in Table 4.

TABLE 4

Treatment of silicon resin and hexamethyldisiloxane with tap water in an apparatus comprising glass fibers to remove HCl.

| Water flow rate (g/min) | Silicone flow rate (g/min) | Flow rate ratio silicone:water | Fiber content in conduit | Residence time (min.) | HCl removal efficiency (%) |
|---|---|---|---|---|---|
| 1.4 | 3.8 | 2.7:1 | 145,000 | 8 | 99.9 |
| 1.6 | 4 | 2.5:1 | 73,000 | 9 | 99.2 |
| 1 | 4 | 4:1 | 145,000 | 8 | 99.9 |

Example 4

The same apparatus, reactants and procedure were used as in example 3 except that the Teflon-FEP conduit measured only 14 cm in length, and 10 cm of the fibers extended out of the downstream end of the conduit and into the collection vessel. The parameters were varied as listed in Table 5.

TABLE 5

Treatment of silicon resin and hexamethyldisiloxane with tap water in an apparatus comprising glass fibers to remove HCl.

| Water flow rate (g/min) | Silicone flow rate (g/min) | flow rate ratio silicone:water | Fiber content in conduit | Residence time (min.) | HCl removal efficiency (%) |
|---|---|---|---|---|---|
| 1.6 | 4.1 | 2.6:1 | 145,000 | 4.5 | 97.9 |
| 1.4 | 3.7 | 2.6:1 | 74,000 | 4.6 | 96.4 |

Example 5

Apparatus, reactants and procedure similar to those described in example 3 were used in this example except xylene was used to dilute the silicon resin to 50% (w/w) instead of hexamethyldisiloxane and the second liquid contained an acetate salt. Samples of the silicon resin, before and after treatment, were analyzed by Ion Chromatography (IC) and indicated that over 92% of all ionic species were removed from the silicon resin.

Example 6

This example illustrates the use of a apparatus according to FIG. 1 to treat a dimethylsiloxane stream with deionized water to remove hydrochloric acid from the dimethylsiloxane. The apparatus of this example comprised a 0.95 cm nominal inner diameter Teflon® PFA (Copolymer of Tetrafluoro Ethylene and Perfluoroalkyl Vinyl Ether) conduit of length 57.15 cm containing approximately 1,500 hydrophobic Teflon® PTFE (Polytetrafluoroethylene) Fluoropolymer Fiber Multifilament Yarns [Toray Fluoropolymers America Inc. (TFA)]. The fibers were 15.355 µm in diameter, approximately 58 cm in length, packed along the entire length of the conduit, and had approximately 1 cm extending out of the downstream end of the conduit into a separatory funnel. A 1.27 cm diameter Teflon® PFA tee was attached to the inlet end of the conduit and deionized water and dimethylsiloxane feed lines attached.

Dimethylsiloxane (15 cSt at 25° C. and comprising 55% cyclic siloxane and 45% hydroxyl endblocked linear polydimethylsiloxane with a number average molecular weight equal to about 2,500) containing HCl was introduced into the apparatus conduit at the upstream end of the Teflon® PTFE fluoropolymer fibers as the first liquid. After the dimethylsiloxane flow was started, a second liquid comprising of DI (Deionized) water was introduced into the conduit at the upstream end of the fibers through the side inlet of the tee. The dimethylsiloxane first liquid and DI water second liquid were collected in the separatory funnel at the downstream end of the fibers. Five experimental runs were performed varying the contact time. The flow rate ratio of the dimethylsiloxane to DI water was kept constant at 4:1. The DI water and dimethylsiloxane streams exited the conduit as separate phases. No settling time was required in the separatory funnel as there was instantaneous separation of the polydimethylsiloxane and DI water phases. Samples of the polydimethylsiloxane stream prior to entering the conduit and from the collection vessel were titrated with potassium hydroxide using bromocresol purple indicator to determine the acid concentration. All testing was performed at 25° C. The flow rates, pressures, contact time and HCl removal efficiency are listed in Table 2.

TABLE 6

Treatment of polydimethylsiloxane containing HCl with DI water in an apparatus comprising Teflon ® PTFE (Polytetrafluoroethylene) Fluoropolymer fibers.

| DI Water flowrate (ml/min) | Dimethyl-siloxane flowrate (ml/min) | DI water line pressure (psig) | Dimethyl-siloxane line pressure (psig) | Residence Time (min.) | HCl removal efficiency (%) |
|---|---|---|---|---|---|
| 1 | 4 | 0 | 0.25 | 7.46 | 99.7 |
| 1 | 4 | 0.5 to 0.75 | 0.75 to 1 | 7.46 | 97.0 |
| 1 | 4 | 0.5 | 0.75 | 7.46 | 98.6 |
| 2 | 8 | 1 | 2 to 3 | 3.73 | 96.2 |
| 4 | 16 | 2 | 4 to 5 | 1.87 | 96.0 |

Example 7

This example illustrates the use of a apparatus according to FIG. 1 to treat a siloxane stream containing cyclic siloxane species with an organic solvent system to remove cyclic siloxane from the siloxane stream. The apparatus of this example comprised a 0.95 cm nominal inner diameter fluorinated ethylene propylene (FEP) Teflon conduit of length 53.34 cm containing approximately 168,000 Glass Wool Pyrex® fibers (Product #CLS3950-454G, Sigma-Aldrich Co., St. Louis, Mo.). The fibers were 8 µm in diameter, approximately 63.5 cm in length, packed tightly along the entire length of the conduit, and had approximately 10 cm extending out of the downstream end of the conduit into a separatory funnel. A 0.95 cm FEP Teflon tee was attached approximately 11.4 cm from the inlet end of the conduit. 10% water in methanol (v/v) was attached at the inlet of the apparatus and siloxane stream containing cyclic siloxane species was introduced at the tee.

Methanol containing 10% (w/w) water, based on the weight of the methanol and water, flow was introduced into the apparatus conduit at the upstream end of the Pyrex® glass fibers as the first liquid. After the 10% water in methanol was started, a second liquid comprising of approximately 1.6 weight percent Octamethylcyclotetrasiloxane (D4 cyclic) in 50 censtistoke trimethyl endblocked polydimethylsiloxane was introduced into the conduit through the side inlet of the tee, contacting the fibers. The 10% water in methanol, first liquid, and siloxane species, second liquid, were collected in the separatory funnel at the downstream end of the fibers. The flow rate ratio of the cyclic containing siloxane to 10% water in methanol solvent was 3:1. No settling time was required in the separatory funnel as there was instantaneous separation of the siloxane (more dense phase) and 10% water in methanol (less dense phase) phases. Samples of the siloxane stream were analyzed by gas chromatography to determine the cyclic concentration prior and after the apparatus. All testing was performed at 25° C. The flow rate, pressure, contact time and cyclic material removal efficiency is listed in Table 2.

TABLE 7

Treatment of siloxane species contaminated with cyclic material with 10% water in methanol in an apparatus comprising glass fibers.

| Nominal 10% methanol flowrate (g/min) | Nominal Cyclic siloxane in linear siloxane flow rate (g/min) | Back pressure (psig) | Residence Time (min.) | Inlet Concentration of cyclic siloxane in linear siloxanes (weight %) | Outlet Concentration of cyclic siloxane in linear siloxanes (weight %) | D4 Cyclic material removal efficiency (%) |
|---|---|---|---|---|---|---|
| 3.5 | 1.5 | 20 | 9 | 1.73 | 1.34 | 22.5 |

Example 8

This example illustrates the use of apparatus according to FIG. 1 to treat a cyclic methylhydrogen siloxane in an isoalkane stream (30% (w/w) siloxane and 70% (w/w) isoalkane) with deionized water to remove hydrochloric acid from the cyclic methylhydrogen siloxane. The apparatus in this example comprised of a 1.27cm nominal inner diameter Teflon® PFA conduit of length 30.48 cm containing approximately 65,000 glass Wool Pyrex fibers (Catalog #34552-01, Cole-Palmer, London, UK). The fibres were 8 µm in diameter, approximately 41 cm in length, packed tightly along the entire length of the conduit, and had approximately 10 cm extending out of the downstream end of the conduit into a separator vessel. A 1.27 cm Teflon® tee was attached to the inlet end of the conduit and deionized water and cyclic methylhydrogen siloxane feed lines attached. The DI water first liquid and cyclic methylhydrogen siloxane second liquid were collected in the separator vessel at the downstream end of the fibers. Experimental runs were performed varying the contact time, during which the flow rate ratio of the cyclic methylhydrogen siloxane to DI water was varied as listed in Table 8 below.

The DI water and cyclic methylhydrogen siloxane streams exited the conduit as separate phases. No settling time was required in the separator vessel as there was instantaneous separation of the cyclic methylhydrogen siloxane and water phases. Samples of the cyclic methylhydrogen siloxane stream prior to entering the conduit were titrated with potassium hydroxide using bromocresol purple indicator to determine the acid concentration. Samples of the cyclic methylhydrogen siloxane siloxane stream from the separator vessel were analysed using ion chromatography to determine the acid concentration. All testing was performed at 25° C. The flow rates, contact time and HCl removal efficiency are listed in the table below:

TABLE 8

Treatment of cyclic methylhydrogen siloxane with deionized water in an apparatus comprising glass fibres to remove HCl.

| Silicone flow rate (ml/min) | Water flow rate (ml/min) | Flow rate ratio silicone:water | Residence time (min.) | HCl removal efficiency (%) |
|---|---|---|---|---|
| 1 | 1 | 1:1 | 18.8 | 99.9 |
| 4 | 1 | 4:1 | 7.5 | 99.9 |
| 8 | 1 | 8:1 | 4.2 | 99.9 |
| 16 | 1 | 16:1 | 2.2 | 99.7 |
| 1 | 4 | 1:4 | 7.5 | 99.9 |
| 2 | 8 | 1:4 | 3.8 | 99.9 |

Example 9

The apparatus, reactants and procedure were the same as described in example 8 with the exception that hydrochloric acid (Catalog #A466-250, Fischer Scientific, Loughborough, UK) of 32%wt was used instead of deionized water. Varying concentrations were made up by diluting with deionized water. The parameters are varied as indicated in the table below:

TABLE 9

Treatment of cyclic methylhydrogen siloxane with hydrogen chloride (aq) in an apparatus comprising glass fibres to remove HCl.

| HCl (aq) strength (% wt) | Silicone flow rate (ml/min) | HCl (aq) flow rate (ml/min) | Flow rate ratio silicone:water | Residence time (min.) | HCl removal efficiency (%) |
|---|---|---|---|---|---|
| 1% | 4 | 1 | 4:1 | 7.5 | 99.8 |
| 2% | 4 | 1 | 4:1 | 7.5 | 99.9 |
| 5% | 4 | 1 | 4:1 | 7.5 | 99.9 |
| 10% | 4 | 1 | 4:1 | 7.5 | 99.4 |
| 20% | 4 | 1 | 4:1 | 7.5 | 99.9 |
| 32% | 4 | 1 | 4:1 | 7.5 | 97.4 |

Example 10

The reactants and the procedure are the same as described in example 8. The apparatus in this example is comprised of a 3.81cm nominal inner diameter glass conduit of length 40.64 cm containing approximately 585,000 glass Wool Pyrex fibers and had approximately 20 cm extending out of the downstream end of the conduit into a separator vessel. A 3.81 glass tee was attached to the inlet end of the conduit and deionized water and cyclic methylhydrogen siloxane feed lines attached. The flow rates, contact time and HCl removal efficiency are listed in the table below:

TABLE 10

Treatment of cyclic methylhydrogen siloxane with deionized water in an apparatus comprising glass fibres in a conduit of 3.81 cm inner diameter to remove HCl.

| Silicone flow rate (ml/min) | HCl (aq) flow rate (ml/min) | Flow rate ratio silicone:water | Residence time (min.) | HCl removal efficiency (%) |
|---|---|---|---|---|
| 68 | 17 | 4:1 | 5.3 | 99.9 |
| 136 | 34 | 4:1 | 2.6 | 99.9 |

That which is claimed is:

1. A process for removing an impurity from a siloxane, the process comprising:
   i) flowing a first liquid through a fiber bundle comprising a plurality of fibers extending lengthwise in a conduit, wherein the bundle has an upstream end and a downstream end, and the first liquid flows in a direction from the upstream end of the bundle to the downstream end; and
   ii) while continuing (i), flowing a second liquid comprising a siloxane and an impurity through the fiber bundle in a direction from the upstream end of the bundle to the downstream end of the bundle to effect transfer of at least a portion of the impurity from the second liquid to the first liquid, wherein the first liquid and the second liquid are substantially immiscible.

2. The process of claim 1, further comprising (iii) receiving the first liquid and the second liquid in a collection vessel, wherein the first liquid forms a first layer and the second liquid forms a second layer in the collection vessel.

3. The process of claim 1, wherein the siloxane is a silicone fluid or silicon resin.

4. The process of claim 1, wherein the impurity is an acid, a salt, or an ion.

5. The process of claim 4, wherein the impurity is an acid selected from hydrogen chloride, hydrogen bromide, hydrogen fluoride, hydrogen iodide, and trifluoromethane sulfonic acid.

6. The process of claim 5, wherein the impurity is hydrogen chloride.

7. The process of claim 4 wherein the impurity is sodium chloride.

8. The process of claim 4 wherein the impurity is a chloride ion.

9. The process of claim 1, wherein the second liquid comprises from 50 to 1,500 ppmw of the impurity.

10. The process of claim 1, wherein the first liquid and second liquid are at a temperature from 15 to 60 ° C.

11. The process of claim 1, wherein the fibers comprise cotton, jute, silk, treated minerals, untreated minerals, metals, metal alloys, treated carbon, untreated carbon, polymers, or polymer blends.

12. The process of claim 11, wherein the fibers are glass or steel fibers.

13. The process of claim 1, wherein the first liquid comprises water.

14. The process of claim 1, wherein the siloxane is formed by the hydrolysis of $R_aSiX_{4-a}$, wherein each R is independently H or a monovalent organic group, X is $C_1$—$C_8$ alkoxy or halo, and a is an integer from 0 to 3.

15. The process according to claim 14, wherein each R is independently methyl or hydrogen and X is chloro.

16. The process of claim 1, wherein the volumetric flow ratio of the second liquid to the first liquid is from 1 to 4.

17. The process of claim 1, wherein the fibers have a diameter from 5 to 25µm.

18. The process of claim 1, wherein the first liquid and second liquid have a residence time from 5 seconds to 30 minutes.

19. The process of claim 1, wherein the second liquid further comprises a non-polar solvent.

20. The process of claim 1, wherein the first liquid has a viscosity from 0.1 to 100 cSt, at 25 ° C., and wherein the second liquid has a viscosity from 0.1 to 100 cSt, at 25 ° C.

21. The process of claim 13, wherein the first liquid is aqueous HCl.

* * * * *